United States Patent [19]

Duggan

[11] 3,974,221

[45] Aug. 10, 1976

[54] PROCESS FOR PREPARING CYCLOHEXANONE FROM CYCLOHEXANOL

[75] Inventor: Raymond J. Duggan, West Seneca, N.Y.

[73] Assignee: Allied Chemical Corporation, Morris Township, N.J.

[22] Filed: Oct. 28, 1970

[21] Appl. No.: 84,902

[52] U.S. Cl............................ 260/586 P; 260/631 R
[51] Int. Cl.²................. C07C 27/12; C07C 45/02; C07C 45/16
[58] Field of Search .............................. 260/586 B

[56] References Cited
UNITED STATES PATENTS

| | | | |
|---|---|---|---|
| 2,223,494 | 12/1940 | Loder ................................ | 260/586 |
| 2,223,500 | 12/1940 | Scott et al........................... | 260/586 |
| 2,285,914 | 6/1942 | Drossbach ......................... | 260/586 |

*Primary Examiner*—Norman Morgenstern
*Attorney, Agent, or Firm*—Michael S. Jarosz

[57] ABSTRACT

A process for preparing cyclohexanone by oxidizing cyclohexanol with a molecular oxygen-containing gas in the presence of a metal catalyst under pressure at elevated temperatures. The process is highly selective for the preparation of cyclohexanone.

5 Claims, No Drawings

PROCESS FOR PREPARING CYCLOHEXANONE FROM CYCLOHEXANOL

This application relates to the preparation of cyclohexanone. More particularly, this application relates to a process for preparing cyclohexanone by oxidation of cyclohexanol.

DESCRIPTION OF THE PRIOR ART

Cyclohexanone is a valuable precursor for the preparation of ε-caprolactam. It is generally prepared by liquid phase oxidation of cyclohexane with air or other oxygen-containing gas, generally in the presence of a metal catalyst. However this reaction produces a variety of oxidation products in addition to the desired cyclohexanone, such as cyclohexanol, hydroxy acids, diacids, esters and higher molecular weight products. By proper control of the reaction conditions, the reaction can be conducted to produce cyclohexanone and cyclohexanol as the principal products of the oxidation.

In order to increase the overall yield of cyclohexanone, various processes have been suggested to convert the cyclohexanol to cyclohexanone. This can be done by dehydrogenation of cyclohexanol in the vapor phase in the presence of appropriate metal catalysts, but other by-products are also obtained which substantially decrease the overall yield of cyclohexanone. Other methods suggested are limited oxidation of cyclohexanol in the absence of a catalyst, but the yield is low, the reaction is slow, and adipic acid is also formed in substantial yield.

SUMMARY OF THE INVENTION

It is an object of the present invention to provide an improved process for the conversion of cyclohexanol to cyclohexanone.

It is another object to provide a process for converting cyclohexanol to cyclohexanone in high yields in a rapid process with a minimum formation of by-products.

Other objects will be apparent from the following detailed description thereof.

According to the present process, cyclohexanol can be oxidized with a molecular oxygen-containing gas at elevated temperatures and pressures in the presence of a metal catalyst to form cyclohexanone in high yield in a rapid and simple process readily adaptable to commercial operation. Conversion of over 90% of the cyclohexanol to cyclohexanone is obtained, indicating a very high selectivity for the reaction under the present conditions, with a minimum formation of other oxidation products.

DETAILED DESCRIPTION OF THE INVENTION

A reaction mixture of cyclohexanol and an insoluble metal catalyst are charged to a pressure reactor fitted with inlet and outlet gas lines, an impeller or other means of agitation to ensure good contact between the reaction mixture and the molecular oxygen-containing gas, a condenser and means of heating. The reaction mixture is brought up to the desired oxidation temperature and the molecular oxygen-containing gas feed begun. When the desired degree of oxidation has been reached, the reaction is stopped and the cyclohexanone recovered.

The cyclohexanol starting mixture should be essentially free of solvents such as cyclohexane, but may contain trace quantities of solvents, catalyst residues, other oxidation by-products of cyclohexane and the like.

Metal catalysts suitable for use in the present process include salts of metals of variable valence which are insoluble in cyclohexanol and cyclohexanone. Illustrative metals are cobalt, manganese, cerium, iron, nickel, lead, titanium, vanadium, chromium, molybdenum, uranium, platinum and silver. The preferred metals are cobalt and manganese. Suitable salts of these metals include their oxides, hydroxides, carbonates, halides, sulfates, phosphates, tungstates, chromates, vanadates and molybdates. The preferred salts are the oxides and carbonates. The metal salt catalysts may be supplied conveniently on a suitable inorganic carrier, such as silica, alumina, carbon, etc. The amount of catalyst present can vary from about 0.2 to 5.0% by weight of the cyclohexanol, and preferably from about 0.5 to 1.5% by weight will be employed.

Suitable molecular oxygen-containing gases include air and other mixtures of oxygen and inert gases such as nitrogen or helium. The molecular oxygen should be supplied to the reaction mixture at a rate sufficient to ensure economic rates of reaction. If an insufficient amount of oxygen is supplied, the initiation period for the reaction will also be unduly lengthened. Improved results are obtained when the molecular oxygen-containing gas is essentially anhydrous. This can be done by passing the feed gas over a dessicant, or by supercooling to a −50°F. dewpoint.

The temperature range of the reaction can vary from about 145° to 210°C. The preferred temperature range is from about 160°–190°C. At lower temperatures, adipic acid rather than the desired cyclohexanone will be formed. The reaction is conducted under pressures of from about 60 to 225 psig, preferably 100–160 psig.

The reaction vessel is vented to remove water as it formed, suitably through a condenser. The condensate can be conducted to a phase separator wherein the water of reaction can be separated in known manner from any condensed starting material which can be recycled to the reaction.

A period of initiation is generally required for the reaction, usually from about 15–30 minutes, depending upon the oxygen feed rate, temperature, pressure and the like. Thereafter the reaction proceeds rapidly. Conversion of the starting material increases with time, but as the relative amount of cyclohexanol to cyclohexanone decreases, the overall conversion to cyclohexanone decreases, and other oxidation products will also be obtained in increasing amounts.

Cyclohexanone is recovered from the reaction mixture by removing the insoluble catalyst, as by filtration or other suitable means known to one skilled in the art, and separating the cyclohexanone product from unreacted starting material and other oxidation products in conventional manner, as by fractional distillation. The unreacted feedstock can be recycled. Although the above description has been given with respect to a batchtype operation, the process is adaptable to continuous operation, as will be known to the skilled art worker.

The invention will be further illustrated by the following examples, but it is to be understood that the invention is not meant to be limited to the details described therein. In the examples, yields are given as mols of cyclohexanone based on mols of cyclohexanol consumed. All parts and percentages are by weight.

EXAMPLE 1

1000 Parts of cyclohexanol containing 1.0% of cobalt carbonate on silica as catalyst were charged to an agitated batch reactor fitted with gas inlet and outlet, a condenser, and heating means. The reaction mixture was heated to 180°C. under 140 psig pressure. Air which had been dried by cooling to −50°F. was then fed to the reactor at a rate of 8 scft. After about fifteen minutes, oxygen began to be absorbed by the reaction mixture.

Reaction was continued for about 45 minutes when a sample of the reaction mixture was withdrawn. About 15–20% of the cyclohexanol had been consumed. The oxidation product was 95–98% cyclohexanone.

The reaction was continued for a total of 180 minutes. About 40–50% of the cyclohexanol had been consumed, and 90–92% of the product was cyclohexanone.

EXAMPLE 2

For purposes of comparison, the procedure of Example 1 was followed except using mixtures of cyclohexane and cyclohexanol as starting material. The initiation period was increased to 30–40 minutes and the conversion and yield decreased. The data are summarized below wherein A is a 50:50 mixture of cyclohexane and cyclohexanol, and B is a mixture of cyclohexane containing 25% of cyclohexanol.

|   | Reaction Time, Minutes | Yield of Cyclohexanone |
|---|---|---|
| A | 90 | 84.5 |
|   | 120 | 79.0 |
|   | 240 | 62.7 |
| B | 90 | 55.0 |

I claim:

1. Process for the selective conversion of cyclohexanol to cyclohexanone which comprises heating cyclohexanol containing from 0.5 to 1.5 percent by weight of cobalt carbonate at a temperature from 145°–210°C. under pressure of 60–225 psig, introducing a molecular oxygen-containing gas and continuing the reaction so that over 90 percent by weight of the reacted cyclohexanol has been converted to cyclohexanone and recovering the cyclohexanone.

2. Process for the selective conversion of cyclohexanol to cyclohexanone which comprises heating cyclohexanol containing from 0.5 to 1.5 percent by weight of cobalt carbonate to a temperature from 160°–190°C. under pressure of 100–160 psig, introducing a molecular oxygen-containing gas and continuing the reaction under substantially anhydrous conditions so that over 90 percent by weight of the reacted cyclohexanol has been converted to cyclohexanone and recovering the cyclohexanone.

3. Process for the conversion of cyclohexanol to cyclohexanone which comprises heating cyclohexanol containing from 0.2 to 5.0 percent by weight of cobalt carbonate at a temperature from 145°–210°C. under pressure of 60–225 psig, introducing a molecular oxygen-containing gas and continuing the reaction so that over 90 percent by weight of the reactive cyclohexanol has been converted to cyclohexanone and recovering the cyclohexanone.

4. The process of claim 3 wherein the molecular oxygen containing gas is essentially anhydrous.

5. The process of claim 3 wherein by-product water is removed continuously during the reaction.

* * * * *